United States Patent
Steinle et al.

(10) Patent No.: US 9,911,187 B2
(45) Date of Patent: Mar. 6, 2018

(54) DETERMINING A STRAIGHT LINE TRAJECTORY FOR A MEDICAL PROCEDURE

(71) Applicant: Brainlab AG, Munich (DE)

(72) Inventors: Wolfgang Steinle, Munich (DE); Christoffer Hamilton, Aschheim (DE); Nils Frielinghaus, Heimstetten (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 15/535,958

(22) PCT Filed: Sep. 3, 2015

(86) PCT No.: PCT/EP2015/070153
§ 371 (c)(1),
(2) Date: Jun. 14, 2017

(87) PCT Pub. No.: WO2017/028934
PCT Pub. Date: Feb. 23, 2017

(65) Prior Publication Data
US 2017/0348056 A1    Dec. 7, 2017

Related U.S. Application Data

(63) Continuation of application No. PCT/EP2015/069037, filed on Aug. 19, 2015.

(51) Int. Cl.
*G06T 7/00* (2017.01)
*A61B 34/10* (2016.01)
(Continued)

(52) U.S. Cl.
CPC ............ *G06T 7/0012* (2013.01); *A61B 34/10* (2016.02); *B25J 9/1666* (2013.01); *G06T 7/70* (2017.01);
(Continued)

(58) Field of Classification Search
CPC .............. A61B 34/10; A61B 2034/105; A61B 2034/107; A61B 2090/364;
(Continued)

(56) References Cited

U.S. PATENT DOCUMENTS 5,279,309 A * 1/1994 Taylor ................. B25J 9/04
600/595
5,445,166 A * 8/1995 Taylor ................. B25J 9/04
128/897
(Continued)

FOREIGN PATENT DOCUMENTS

WO    WO 2014019714 A2    2/2014
WO    WO 2014139024 A1    9/2014

OTHER PUBLICATIONS

International Search Report and Written Opinion, PCT/EP2015/070153, dated May 18, 2016.

*Primary Examiner* — Manav Seth
(74) *Attorney, Agent, or Firm* — Middleton Reutlinger

(57) ABSTRACT

Disclosed is a computer-implemented method for planning a trajectory (11) through an anatomical body part (1), the trajectory (11) being usable for a medical procedure and the method comprising executing on at least one processor of at least one computer, steps of: •a) acquiring (S1), at a processor, patient image data describing a medical image of a patient anatomical body part being the anatomical body part (1) in a patient's body. •b) acquiring (S2), at a processor, atlas trajectory data describing a model anatomical body part being a model of the patient anatomical body part, and describing the position of at least one predetermined trajectory through the model anatomical body part; •c) acquiring (S3), at a processor, critical structure data describing the position of at least one critical structure (5) in the model anatomical body part or in the patient anatomical body part; •d) determining (S4), by a processor and based on the patient
(Continued)

image data and the atlas trajectory data and the critical structure, mapping data describing a mapping of the model anatomical body part, of the position of the at least one predetermined trajectory and of the position of the at least one critical structure (5) onto the medical image of the patient anatomical body part; •e) determining (S5), by a processor and based on the mapping data and the atlas trajectory data and the patient image data, analysis region data describing an analysis region in the patient image data, the analysis region (16) having a position in the patient anatomical body part fulfilling a predetermined spatial condition relative to the position of the mapped predetermined trajectory (6); •f) determining (S6), by the processor and based on the patient image data and the atlas trajectory data and the analysis region data and the critical structure data, straight trajectory data describing a straight line trajectory (11) through the patient anatomical body part having a position fulfilling a predetermined spatial condition relative to the position of at least one critical structure (5) in the patient anatomical body part.

13 Claims, 3 Drawing Sheets

(51) Int. Cl.
*G06T 7/70* (2017.01)
*G06T 11/00* (2006.01)
*B25J 9/16* (2006.01)
*A61B 90/00* (2016.01)
*A61N 5/10* (2006.01)
*A61B 10/02* (2006.01)

(52) U.S. Cl.
CPC ......... *G06T 11/001* (2013.01); *A61B 10/0233* (2013.01); *A61B 90/37* (2016.02); *A61B 2034/105* (2016.02); *A61B 2034/107* (2016.02); *A61B 2090/364* (2016.02); *A61B 2090/365* (2016.02); *A61N 5/1049* (2013.01); *A61N 2005/1059* (2013.01); *G06T 2207/10024* (2013.01); *G06T 2207/10028* (2013.01); *G06T 2207/10081* (2013.01); *G06T 2207/10088* (2013.01); *G06T 2207/30024* (2013.01); *G06T 2207/30241* (2013.01)

(58) Field of Classification Search
CPC .............. A61B 2090/365; A61B 90/37; A61B 10/0233; G06T 7/70; G06T 7/0012; G06T 11/001; G06T 2207/10024; G06T 2207/10028; G06T 2207/10081; G06T 2207/10088; G06T 2207/30024; G06T 2207/30241; B25J 9/1666; A61N 5/1049; A61N 2005/1059
See application file for complete search history.

(56) References Cited

U.S. PATENT DOCUMENTS

| | | | | |
|---|---|---|---|---|
| 5,622,170 | A * | 4/1997 | Schulz | A61B 5/0064 356/141.1 |
| 5,797,849 | A * | 8/1998 | Vesely | A61B 5/0422 600/461 |
| 5,987,349 | A * | 11/1999 | Schulz | A61B 5/0064 356/141.1 |
| 6,016,439 | A * | 1/2000 | Acker | A61B 5/06 600/411 |
| 6,434,415 | B1 * | 8/2002 | Foley | A61B 5/0064 600/425 |
| 6,690,964 | B2 * | 2/2004 | Bieger | A61B 90/36 600/407 |
| 7,880,154 | B2 * | 2/2011 | Otto | A61N 5/103 250/492.3 |
| 8,170,716 | B2 * | 5/2012 | Coste-Maniere | B25J 9/1671 128/897 |
| 8,442,621 | B2 * | 5/2013 | Gorek | A61B 17/7091 600/424 |
| 2005/0075578 | A1 * | 4/2005 | Gharib | A61B 5/0492 600/546 |
| 2009/0259230 | A1 | 10/2009 | Khadem et al. | |
| 2014/0003696 | A1 | 1/2014 | Taghva | |

* cited by examiner

DETERMINING A STRAIGHT LINE TRAJECTORY FOR A MEDICAL PROCEDURE

The present invention is directed to a computer-implemented method for planning a trajectory through an anatomical body part, a corresponding computer program, a non-transitory program storage medium storing such a program and a system comprising a computer for executing the program, as well as a medical procedure planning system comprising a database and such a computer.

TECHNICAL BACKGROUND

Conventionally, the trajectory is calculated based on anatomical structures identified automatically (e.g. with an atlas) combined with a scoring that favours short trajectories (for example, a trajectory having a minimal distance between entry point and target region).

However, this is a theoretical calculation that ignores real-world considerations when placing a trajectory. Examples of this are patient positioning during surgery and aesthetic reasons (e.g. a trajectory entry in a sensitive part of the face). Further, the calculations do not consider current best practice trajectory placement. For example, these approaches ignore the fact that the planned trajectory having the minimum distance between entry point and target region may endanger an organ-at-risk, or that the planned trajectory may not be a straight line which for some applications such as insertion of a relatively rigid biopsy needle or emission of a beam of ionizing treatment radiation along the planned trajectory is essential.

An object of the invention therefore is to provide a method of planning a straight line trajectory for use in a medical procedure which considers both the necessities of the envisaged medical procedure and the positions of organs-at-risk.

Aspects of the present invention, examples and exemplary steps and their embodiments are disclosed in the following. Different advantageous features can be combined in accordance with the invention wherever technically expedient and feasible.

EXEMPLARY SHORT DESCRIPTION OF THE PRESENT INVENTION

In the following, a short description of the specific features of the present invention is given which shall not be understood to limit the invention only to the features or a combination of the features described in this section.

The disclosed method encompasses determining, from knowledge about a predetermined straight line trajectory relative to a predetermined model of an anatomical body part, a straight line trajectory suitable for example for planning a trajectory suitable for example for insertion of a biopsy needle into a corresponding anatomical body part of a specific patient or the trajectory of a beam of ionising treatment radiation through the corresponding anatomical body part of the patient. To this end, a search region is defined around a mapping of the predetermined trajectory onto medical image data representing the corresponding anatomical body part of the patient. The search area is analysed for potentially feasible straight line trajectories through and/or into the anatomical body part of the patient which avoid critical structures (such as organs-at-risk) at least to a predetermined extent.

GENERAL DESCRIPTION OF THE PRESENT INVENTION

In this section, a description of the general features of the present invention is given for example by referring to possible embodiments of the invention.

In general, the invention reaches the aforementioned object by providing, in a first aspect, a computer-implemented method for planning a trajectory through an anatomical body part, the trajectory being usable for a medical procedure. The trajectory may be used as a trajectory for insertion of a biopsy needle, the trajectory of a beam of ionizing radiation for radiotherapy or radiosurgery, as a trajectory for insertion of a catheter for infusion therapy or of a screw during an orthopaedic intervention or of a tool for placing a radioactive seed for brachytherapy or of an ablation instrument for removing tissue. The method comprises executing, on a processor of a computer, steps of the following exemplary steps which are executed by the processor.

In a (for example first) exemplary step, patient image data is acquired which describes (for example defines or represents) a medical image of a patient anatomical body part being the anatomical body part in a patient's body. In other words, the image of patient anatomical body part is a representation of anatomical body part in the real world. The anatomical body part may be any anatomical body part, for example, the head (specifically, at least one of brain and skull), the liver or the lung. The anatomical body part comprises at least one of hard tissue (such as bony tissue or cartilage) and soft tissue (such as the brain, the prostate or a digestive organ such as the stomach, or muscle tissue). The medical image may have been generated before execution of the disclosed method starts, however generation of the medical image may also be part of the disclosed method. The medical image may have been generated or may be generated, respectively, by application of a medical imaging modality (for example, computed x-ray tomography or magnetic resonance tomography) to the anatomical body part. The patient image data may be defined in two or three dimensions. In a specific example, the patient image data is three-dimensional image data and the medical imaging modality applied to the anatomical body part then is a tomographic medical imaging modality.

In a further (for example second) exemplary step, atlas trajectory data is acquired which describes (for example defines or represents) a model anatomical body part being a model of the patient anatomical body part. The model has been generated on the basis of medical image data generated by imaging a plurality of human bodies in one example before the execution of the disclosed method starts. The model of the anatomical body part is defined by for an example an atlas—the general nature of an atlas is defined in the sections "Definitions". The model is defined by positional information associated with colour values, the latter describing tissue types represented in the model, specifically in dependence on the imaging modality used to generate the medical image data from which the model was generated. The imaging was preferably conducted with the same imaging modality as the one used for generating the patient image data. Alternatively, the atlas trajectory data may have been generated with a different imaging modality, and the atlas trajectory data may be made comparable to the patient image data via a multi-modal atlas, i.e. by mapping colour values defining an image of the model to anatomically (i.e. with regard to the depicted tissue type) corresponding colour values in the patient image data using a database of tissue classes corresponding for the respective imaging modalities.

The atlas trajectory data further describes (for example defines or represents) the position of at least one predetermined trajectory through the model anatomical body part. The trajectory in one example is defined as a straight line. For example, at least two sets of coordinates describing (for example defining or representing) two points in a two- or three-dimensional reference system are enough to define the at least two point required to define the position of the trajectory. The trajectory is predetermined in the sense that its position is known prior to execution of the disclosed method. The position is generally gathered from technical literature or expert knowledge about the position of at least one trajectories which are known to be feasible (for example because they connect a target of the envisaged medical procedure with an entry point into the anatomical structure for inserting a medical instrument such as a biopsy needle or catheter, specifically without being close to or crossing a critical structure such as an organ-at-risk). The known position of the predetermined trajectory is acquired by the disclosed method together with the information about the model anatomical body part, and the position of the predetermined trajectory is defined for example in a reference system in which also the positional information of the model of the anatomical body part is defined. However, the information about the position of the predetermined trajectory need not be generated on the basis of medical image information in the sense that a real object defining the trajectory is imaged. The atlas trajectory data describes an association of image colour values with different types of anatomical tissue, and in one example the patient image data describes the medical image as a composition of image colour values on a colour scale comparable (e.g. directly by having the same association between colour values and tissue types or indirectly via a mapping between colour scales in dependence on tissue type to the colour scale used for the image colour values described by the atlas trajectory data. Hence, by establishing a mapping between the positional information defining the positions which define the model anatomical body part and the positional information contained in the patient image data defining the medical image of the patient anatomical body part, the position of the of the predetermined trajectory can be transformed using this mapping into the reference system in which the positional information contained in the patient image data is defined. The mapping can be established for example by applying an image fusion algorithm to the atlas trajectory data and the patient image data to fuse the image-based model of the anatomical body part to the patient anatomical body part defined by the medical image described by the patient image data. The fusion is conducted for example on the basis of comparing colour values (e.g. greyscale values) defining the model of the anatomical body part to grey scale values defining the medical image of the patient anatomical body part in order to establish a mapping between corresponding anatomical structures having comparable (specifically, at least to a predetermined extent the same) colour (e.g. greyscale) values. The mapping is determined by determining the mapping data as described below.

In a further (for example third) exemplary step, critical structure data is acquired which describes (for example defines or represents) the position of at least one critical structure in the model anatomical body part or in the patient anatomical body part. Specifically, the critical structure data comprises information that the position is associated with an anatomical structure which is a critical structure. The critical structure is an organ-at-risk, i.e. an anatomical structure which shall be avoided, for example not be undesirably affected, when conducting the envisaged medical procedure, for example it shall not be negatively influenced by the medical procedure. The critical structure may depend on the medical procedure, and the critical structure data is acquired for example based on information defining the medical procedure. For example, the critical structure is a specific functional area of the brain or a blood vessel in the brain which shall not be traversed by a trajectory along which a biopsy needle is inserted into the brain or which shall have a minimum distance from the opening of a catheter used for dispensing a fluid medication into the brain or which to which no more than a threshold radiation dose shall be applied. The critical structure may also be at least part of another vital anatomical structure such as the liver or the lung which shall be avoided during e.g. radiotherapy. The position of the critical structure may be defined in a reference system used for defining positional information of the model of the anatomical body part or in which positional information used for defining positions of image elements of the patient image data is defined. At least the position of the critical structure is known relative to at least one of those reference systems. The critical structure data may be a subset of the atlas trajectory data, i.e. the position of the at least one critical structure may be defined integrally in the atlas (i.e. the model of the anatomical body part), or it may be acquired as a separate data set, for example as a predetermined (positionally referenced, i.e. defined) data set or on the basis of user input (e.g. by manually outlining using a pointing tool such as mouse an anatomical structure as the critical structure visible in the medical image of the patient anatomical body part). In an even further example, the critical structure may be a specific neural fibre in the brain and the critical structure data may have been generated prior to execution of the disclosed method by fibre tracking executed on medical image data generated by diffusion tensor magnetic resonance imaging (DTI). The critical structure may be detected in the patient image data by an automatic process such as a deformity detection algorithm, for example if the critical structure comprises a tumour which would not be expected in an image of the healthy anatomical body part.

In a further (for example fourth) exemplary step, mapping data is determined which describes (for example defines or represents) a mapping of the model anatomical body part, of the position of the at least one predetermined trajectory and of the position of the at least one critical structure onto the medical image of the patient anatomical body part. The mapping data is determined based on the patient image data and the atlas trajectory data and the critical structure data. The mapping data is determined by applying an image fusion algorithm to the atlas trajectory data and the patient image data, for example by fusing the atlas trajectory data to the patient image data, and for example determining, based on the mapping between the atlas trajectory data and the patient image data, a mapping between the position of the at least one critical structure in the model anatomical body part and a position of at least one corresponding critical structure in the patient anatomical body part. The mapping is for example a transformation (such as a coordinate transformation) and can be represented by a linear transformation matrix which transforms the positional information contained in the patient image data, the atlas trajectory data and the critical structure data onto a common reference system (e.g. coordinate system). In one example, the common reference system into which the positional information is the reference system in which the positional information contained in the patient image data is defined, i.e. the transformation matrix for mapping the positional information contained in the patient image data onto the common reference system may in this example be unity. The mapping is established for example by fusing (e.g. by applying an image fusion algorithm to) the positional information contained in the patient image data, the atlas trajectory data and the critical structure data. The fusing may be elastic or rigid. The mapping is defined by at least the aforementioned matrix and stored as the mapping data for use in at least one subsequent step of the disclosed method.

In a further (for example fifth) exemplary step, analysis region data is determined which describes (for example defines or represents) an analysis region in the patient image data. The analysis region data is determined based on the mapping data and the atlas trajectory data and the patient image data. For example, the position of the predetermined trajectory is mapped by subjecting it to the transformation defined by the mapping data in order to generate what is called herein forth a mapped predetermined trajectory. The position of the mapped predetermined trajectory is in one example defined in the reference system in which the positional information contained in the patient image data is defined. Due to the mapping of the position of the predetermined trajectory into that reference system, the mapped predetermined trajectory may no longer be represented by a straight line but rather a curved line having a curvature which is different from zero in two or three dimensions. However, for some applications in the real world, it will be necessary to determine a straight line trajectory in the patient image data. For example, a biopsy needle or treatment radiation beams follow a generally straight line rather than a true curve. The disclosed method therefore seeks to find at least one feasible straight line trajectory through the patient anatomical body part in a two- or three-dimensional search area around the position of the mapped predetermined trajectory. This search area is herein forth called analysis region. The position of the analysis region in the patient anatomical body part is for example defined such that it fulfils a predetermined spatial condition relative to the position of the mapped predetermined trajectory. The predetermined spatial condition may be defined by the position of the analysis region having a predetermined or calculated spatial extent around the position of the mapped predetermined trajectory and/or by the end points of the mapped predetermined trajectory lying e.g. on the circumference (i.e. an outer limit) of the analysis region. The spatial extent of the analysis region may be determined (for example calculated) as a part of the disclosed method according to for example a predetermined scheme (e.g. by applying a predetermined geometric relationship, i.e. a geometric formula, having as an input quantity for example at least part of the Information defining the position of the mapped predetermined trajectory). The search area may be defined as an envelope along the mapped predetermined trajectory (for example an envelope having a constant distance from the mapped predetermined trajectory or an envelope having a distance from the mapped predetermined trajectory which varies, e.g. Increases, with increasing distance from the end point of the mapped predetermined trajectory lying in the position of the target region). In two dimensions, the analysis region may have the shape of a triangle, and in three dimensions it may have the shape of a pyramid or a cone.

The predetermined spatial condition for the position of the analysis region relative to the position of the mapped predetermined trajectory may be described by analysis region condition data which in one example of the disclosed method is acquired as a step of the disclosed method. The analysis region data may be determined further based on the analysis region condition data.

The straight line trajectory defines a trajectory from a position of the entry point into the patient anatomical body part to a position of the target region in the patient anatomical body part. For example, the predetermined trajectory defines a trajectory from a position of a model entry point, for example an external entry point (i.e. an entry point where trajectory traverses the exterior surface of the model body, e.g. intersects the skull or skin of the model body) or an internal entry point (i.e. an entry point where the trajectory traverses the boundary of the patient anatomical body part).

The model target region corresponds to a target region in the patient anatomical body part comprising a target of the medical procedure. For example, the straight line trajectory is determined by mapping, using the mapping defined by the mapping data, the predetermined trajectory onto the medical image of the patient anatomical body part and determining a straight line lying inside the analysis region having a predetermined distance from the mapped predetermined trajectory and for example at least one critical structure in the patient anatomical body part corresponding to at least one critical structure in the model anatomical body part.

For example, the predetermined trajectory is mapped, using the mapping defined by the mapping data, onto the medical image of the patient anatomical body part and for each incremental point along the mapped predetermined trajectory, an envelope around the mapped predetermined trajectory is determined which has a predetermined distance from the incremental point.

In a first embodiment of this example, a cone is determined as the analysis region in the medical image of the patient anatomical body part, the cone having a conical surface and a tip, wherein the tip of the cone lies at the position of the target region, wherein a straight line connecting the position of the entry point and the position of the target region lies in the conical surface, for example the lateral surface of the cone. Alternatively, the longitudinal axis of the cone (i.e. the axis along the distance connecting the tip and the base surface of the cone) lies on a straight line connecting the position of the entry point and the position of the target region. The cone angle is defined such that the at least one predetermined trajectory lies inside the cone and/or on the conical surface.

In a second embodiment of this example, a pyramid is determined as the analysis region in the medical image of the patient anatomical body part, the pyramid having a pyramidal surface and a tip, wherein the tip of the pyramid lies at the position of the target region, wherein a straight line connecting the position of the entry point and the position of the target region lies in the pyramidal surface, for example the lateral surface of the pyramid. Alternatively, the longitudinal axis of the pyramid (i.e. the axis along the distance connecting the tip of the pyramid and the opposite surface of the pyramid) lies on a straight line connecting the position of the entry point and the position of the target region, and wherein the opening angle of the pyramid at the tip of the pyramid is defined such that the mapped at least one predetermined trajectory lies inside the pyramid and/or on the pyramidal surface.

In a third embodiment of this example, a cone is determined as the analysis region in the medical image of the patient anatomical body part, starting from the position of the target region in the patient anatomical body part and for each incremental point along the mapped predetermined trajectory until the position of the entry point is reached. The cone has a tip lying at the position of the target region and extends at least substantially to an (internal or external, relative to the patient anatomical body part) surface of the patient anatomical body part (i.e. at least so far that the circumference of the base surface of the cone touches the surface) in which the position of the entry point lies, so that the incremental point lies inside the cone and/or on the conical surface.

In a fourth embodiment of this example, a pyramid is determined as the analysis region in the medical image of the patient anatomical body part starting from the position of the target region in the patient anatomical body part and for each incremental point along the mapped predetermined trajectory until the position of the entry point is reached. The pyramid has a pyramidal surface and a tip, the tip lying at the position of the target region and extending at least substantially to an (internal or external, relative to the patient anatomical body part) surface of the anatomical body part (i.e. at least so far that the circumference of the base surface of the pyramid, i.e. the surface lying opposite the tip of the pyramid, touches the surface) in which the position of the entry point lies, so that the incremental point lies inside the pyramid and/or on the pyramidal surface.

Within the framework of all aforementioned examples and embodiments, the position of the straight line may be determined for example by using an optimisation algorithm such as a least squares algorithm which determines its minimum distance from the mapped predetermined trajectory (e.g. for all positions along the mapped predetermined trajectory). As an additional boundary condition for the position of the straight line a minimum distance from the at least one critical structure may be used.

In a further (for example sixth) exemplary step, straight trajectory data is determined which describes (for example defines or represents) a straight line trajectory through the patient anatomical body part having a position fulfilling a predetermined spatial condition relative to the position of the at least one critical structure in the patient anatomical body part. The straight trajectory data is determined based on the patient image data and the atlas trajectory data and the analysis region data and the critical structure data. For example, the analysis region is searched for at least one feasible straight line. This may be done in an iterative process, for example by testing a plurality of sample straight line as to their feasibility. The straight lines may for example be determined by applying a ray-tracing algorithm (also called ray-casting algorithm) to find straight lines embodied by rays which lead from the target region to the entry point into the patient anatomical body part. The camera position of the ray-tracing algorithm may be conveniently located in the target region. The feasible straight line represents a trajectory from the position of the target region which includes a target of the medical procedure (such as tissue to be sampled if the medical procedure is a biopsy or a tumour if the medical procedure is radiotherapy) to an entry point for the medical procedure (e.g. the entry point at which a biopsy needle is first inserted into the anatomical body part or at which a beam of treatment radiation enters the patient anatomical body part). Furthermore, the feasible straight line is determined such that it has a minimum distance from the at least one critical structure. The minimum distance may depend on the nature of the envisaged medical procedure. Specifically, the feasibility of the straight line underlies the boundary conditions that the straight line connects the entry point and the target region and that it fulfils a predetermined spatial condition relative to the position of the at least one critical structure (such as a minimum —for example average—distance from the position of the at least one critical structure or a maximum overlap or intersection with the at least one critical structure). For example, the straight line trajectory may be determined under the boundary condition that it does not intersect parts of the medical image of the patient anatomical body part associated with specific tissue classes defined in the corresponding part of the model of the anatomical body part. For example, a highly parallelizable procedure can be performed on the graphics processing unit by using the ray-tracing algorithm for determining rays as the straight lines, rays are sent from the centre of the target area outwards along all possible trajectories within the cone. For each ray, the tissue classes along the ray are determined by comparing the medical image of the patient anatomical body part to the model anatomical body part. If a ray passes through a critical structure (e.g. a blood vessel), this leads to the ray being invalidated (i.e. declared not feasible for selection as the straight line trajectory). As an alternative our additional boundary condition, the straight line trajectory may be determined such that the distance from the position of its associated entry point to the position of entry point associated with the mapped predetermined trajectory is minimized.

A plurality of straight lines may be determined which would in principle all fulfil the boundary conditions set for their feasibility, albeit to a different extent. These straight lines may be weighted according to the extent to which they fulfil the boundary conditions, and the straight line trajectory may be selected from the plurality of straight lines according to that weighting. For example, if a subset of rays is valid (i.e. constitutes each a feasible straight line), a scoring (weighting) algorithm is used to determine the most promising ray. For example, the weighting may also consider the distance of the straight lines from critical structures of different type, specifically the weighting for fulfillment of this boundary condition may be made dependent on the type of critical structure. For example, a lower distance of the straight line from a more sensitive critical structure may be given a lower weighting so that the associated straight line will be less likely to be selected as the straight lines trajectory. A feasible straight line (specifically, if it is selected as the straight line trajectory) may be fed back to for example a database storing the atlas trajectory data and stored in the atlas trajectory data for later use a predetermined trajectory—this may also be made dependent on how often the respective feasible straight line is selected as the straight line trajectory. This feedback function will lead to a "learning" atlas of predetermined trajectories, and can be made dependent on a confirmation of the feedback into the atlas trajectory data by a user (for example, by command input into a computer executing the disclosed method).

In an embodiment of this sixth step, straight trajectory condition data is acquired which describes (for example defines or represents) the predetermined spatial condition for the position of the straight line trajectory relative to the position of the at least one critical structure in the patient anatomical body part corresponding to the critical structure in the model anatomical body part. The straight trajectory data may be determined further based on the straight trajectory condition data.

Any positional information processed by the disclosed method may be defined in two or three dimensions.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method.

In a third aspect, the invention is directed to a non-transitory computer-readable program storage medium on which the aforementioned program is stored.

In a fourth aspect, the invention is directed to at least one computer (for example, a computer), comprising at least one processor (for example, a processor) and at least one memory (for example, a memory), wherein the aforementioned program is running on the processor or is loaded into the memory, or wherein the computer comprises the aforementioned program storage medium.

In a fifth aspect, the invention is directed to a medical procedure planning system for planning a trajectory through an anatomical body part, the trajectory being usable for a medical procedure, the system comprising:
a) the aforementioned computer; and
b) at least one electronic data storage device (e.g. a non-transitory computer-readable data storage medium) storing at least one database comprising the patient image data, the atlas trajectory data and the critical structure data,
wherein the computer is operably coupled to the at least one database for acquiring, from the at least one database, the patient image data, the atlas trajectory data and the critical structure data.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The method in accordance with the invention is for example a computer implemented method. For example, all the steps or merely some of the steps (i.e. less than the total number of steps) of the method in accordance with the Invention can be executed by a computer (for example, at least one computer). An embodiment of the computer implemented method is a use of the computer for performing a data processing method. The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" Includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the Invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired.

In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Atlas data describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the Image data are compared with the matched atlas in order to assign a point (a pixel or voxel) of the image data to an object of the matched atlas, thereby segmenting the image data into objects.

The present invention relates to the field of controlling a treatment beam. The treatment beam treats body parts which are to be treated and which are referred to in the following as "treatment body parts". These body parts are for example parts of a patients body, i.e. anatomical body parts.

The present invention relates to the field of medicine and for example to planning a trajectory of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/healthcareus_elekta_v-mat.php and http://www.varian.com/us/oncology/treatments/treatment_techniques/rapidarc.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body.

The term "medical imaging methods" is understood to mean (advantageously apparatus-based) imaging methods (so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc.

Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

DESCRIPTION OF THE FIGURES

In the following, the invention is described with reference to the appended figures which represent a specific embodiment of the invention. The scope of the invention is however not limited to the specific features disclosed in the context of the figures, wherein

FIG. 1 illustrates an exemplary sequence of the steps of the above-described method. In step S1, the patient image data is acquired. In step S2, the atlas trajectory data is acquired. Step S3 comprises acquisition of the critical structure data. In step S4, the mapping data is determined as described above on the basis of the patient image data, the atlas trajectory data and the critical structure data. On the basis of the mapping data and the atlas trajectory data and the patient image data, the analysis region is determined in step S5. Step S6 then determines the straight trajectory data on the basis of the patient image data and the atlas trajectory data and the analysis region data and the critical structure data.

FIG. 2 illustrates a two-dimensional section through a realistically three-dimensional arrangement of an anatomical body part 1 being the head, a target region 2 (which may comprise tumour tissue or other tissue which shall be the target of a medical procedure such as a biopsy or radiotherapy/radiosurgery), a critical structure 5, a mapped predetermined trajectory 6, an analysis region 16 and a straight line trajectory 11.

Figure 1:
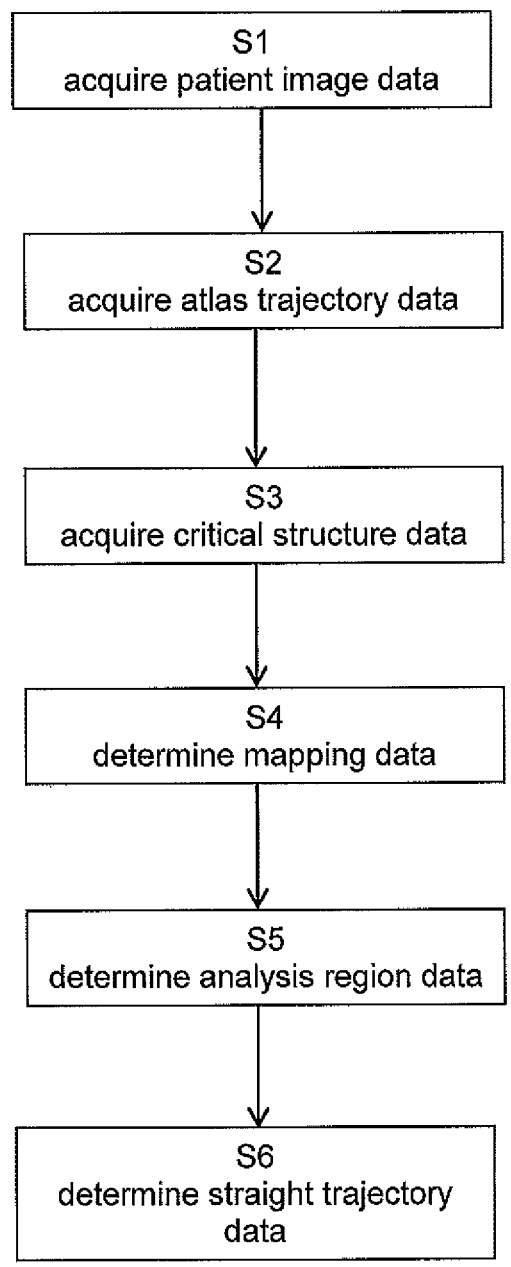
FIG. 1 is flow diagram of the disclosed method.

According to FIG. 2, a basic way is shown for determining a straight line trajectory 11 between a target region 2 having its position at its centre (for example, centre of gravity) 3 (in the following called target centre 3) and an entry point 12 on the exterior surface of anatomical body part 1. The mapped predetermined trajectory 6 is curved having a curvature different from zero and undesirably intersects a critical structure 5, which may be embodied by a blood vessel. In a two-dimensional analysis, a triangle is defined by connecting the centre 3 of the target region 2 and the entry point 4 of the mapped predetermined trajectory 6 with a straight line, and drawing a tangent 15 to the mapped predetermined trajectory 6 in the target centre 3, and drawing a base line 13 between the entry point 4 and the intersection between the tangent 15 and the exterior surface of the anatomical body part (head) 1. In a three-dimensional analysis, a cone or pyramid, respectively, is developed which has the triangle lying (completely) in the external surfaces of the cone or pyramid, respectively. The analysis region 16 is defined as the area of the triangle in two dimensions or the volume of the cone or pyramid, respectively, in three dimensions. The analysis region 16 is searched for (infinite or semi-infinite) straight lines running through the target centre 3 and the exterior surface of the anatomical body part 1. As a boundary condition for selecting one of the determined straight lines as the straight line trajectory, the straight line must keep a minimum distance d from the critical structure 5 and have a minimum average distance from the mapped predetermined trajectory 6. The average distance between the straight line and the mapped predetermined trajectory 6 may be calculated or minimized, respectively, by applying a least squares approach. At least one straight line may be found which may fulfil these conditions. From this result, one of the straight lines is selected as the straight line trajectory 11 either automatically or by user interaction (for example manual selection by a physician after viewing an image display of potentially feasible straight line trajectories). The Intersection of the selected straight line trajectory 11 with the exterior surface of the anatomical body part 1 constitutes the entry point 12 of the straight line trajectory 11. The straight line trajectory 11 may then be used for planning a medical procedure, for example it may be used as trajectory along which a medical instrument such as biopsy probe (biopsy needle) should be inserted to take a tissue sample from the target region 2.

Figure 2:
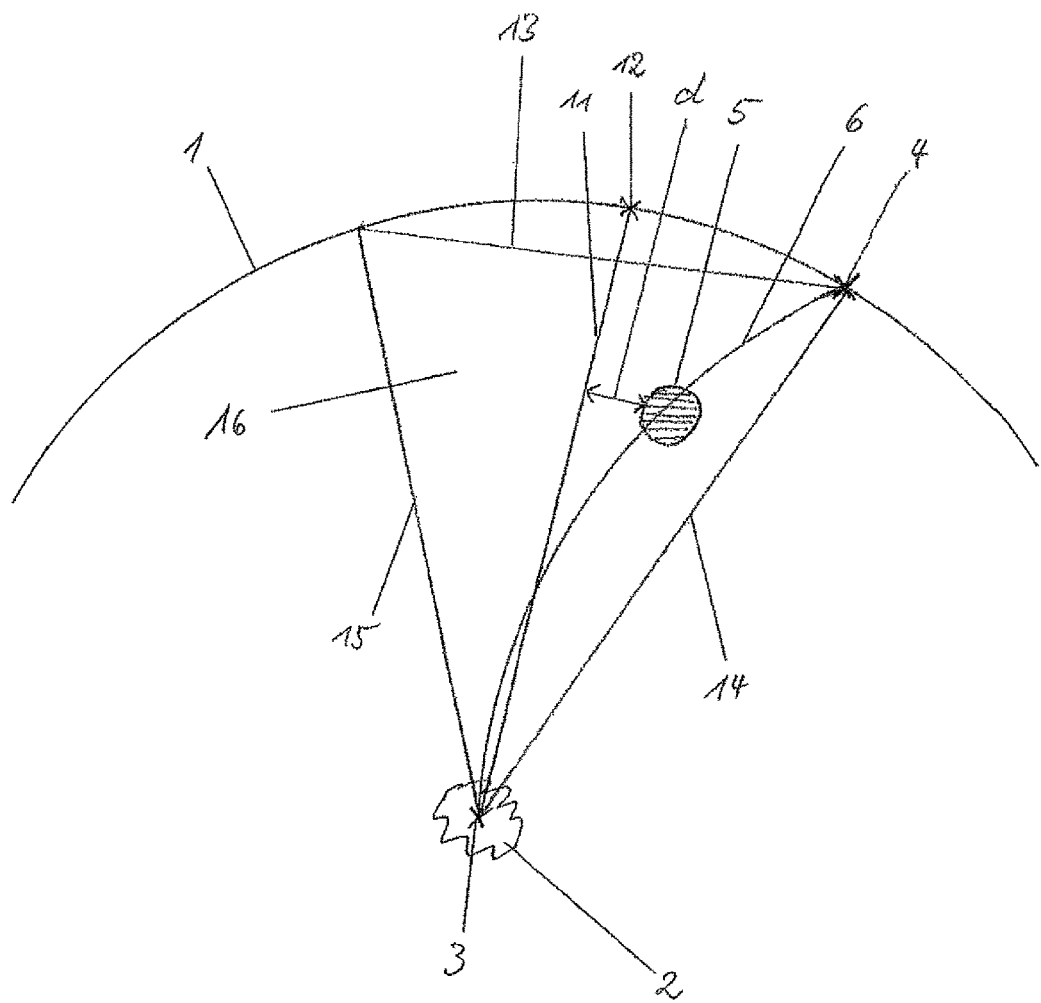
FIG. 2 shows the general definition of a cone or pyramid as an analysis region in a two-dimensional illustration.
Figure 3:
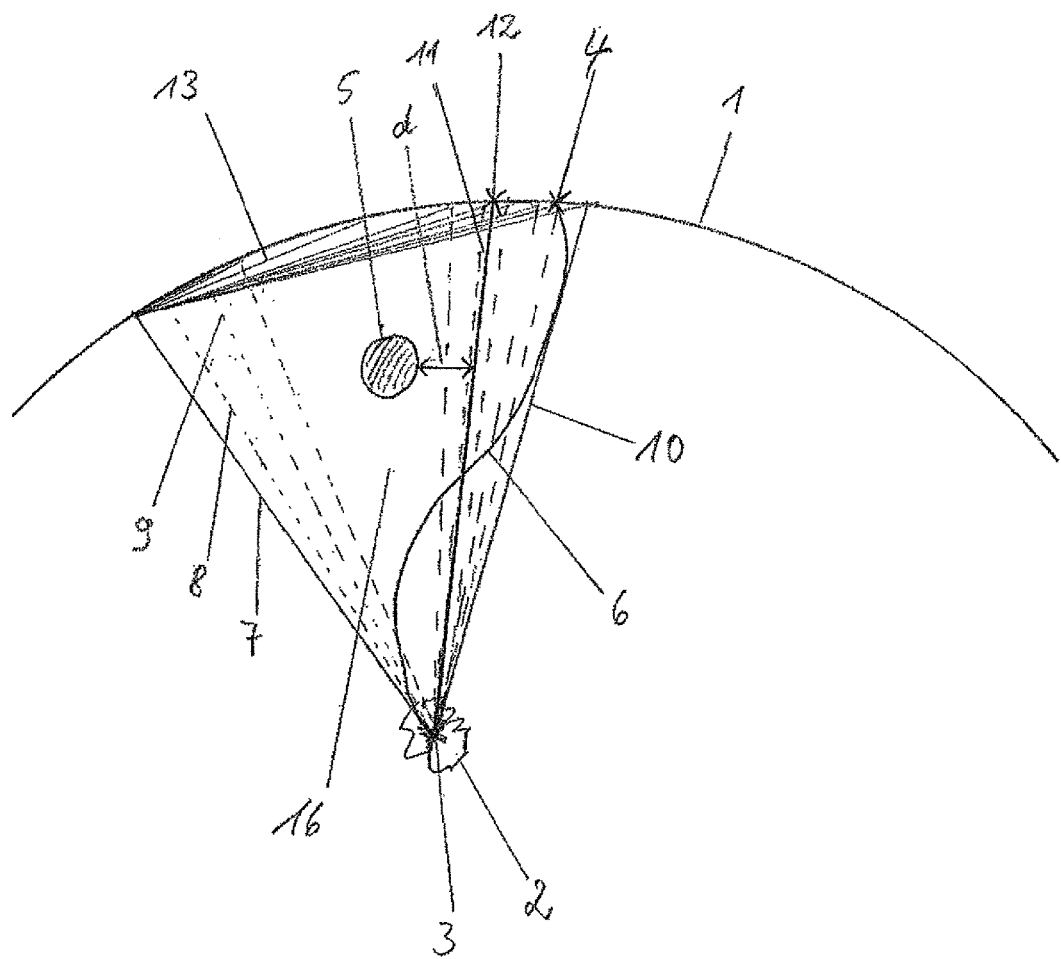
FIG. 3 shows an incremental determination, along the mapped predetermined trajectory, of a cone or pyramid as an analysis region in a two-dimensional illustration.

In FIG. 3, the same reference signs as in FIG. 2 denote the same features. However, FIG. 3 shows a more complex case in which the mapped predetermined trajectory 6 has a non-constant non-zero curvature in two or three dimensions. For example, the mapped predetermined trajectory may be twisted in two or three dimensions. In order to determine a suitable cone or pyramid, respectively, as an analysis region 16 which includes all points along the mapped predetermined trajectory 6, first a tangent 7 to the mapped predetermined trajectory 6 in the target centre 6 is defined. Then, a cone or pyramid, respectively, is defined incrementally for each subsequent point along the mapped predetermined trajectory 6 until its entry point 4 is reached. This cone or pyramid, respectively, is defined such that its volume includes all points along the mapped predetermined trajectory which have so far been analysed (i.e. all points along the mapped predetermined trajectory 6 from the target centre 3 to the incremental point along the mapped predetermined trajectory 6 currently being analysed). The thus incrementally generated straight lines 8, 9 are shown as dashed lines in FIG. 3. The analysis region is defined as the cone or pyramid, respectively, having an opening angle at its tip in the target centre 3 which is (just) large enough so that the volume of cone or pyramid, respectively, accommodates all points of the mapped predetermined trajectory 6. In the example shown in FIG. 3, such a cone or pyramid, respectively, is defined in the two-dimensional illustration of FIG. 3 by straight lines 7, 10 and the base line 13 connecting the intersections of straight lines 7, 10 with the exterior surface of the anatomical body part 1. The straight line trajectory 11 is determined in analogy to the procedure described in connection with FIG. 2.

Further disclosed is a method for visualizing and comparing different feasible straight lines usable as straight line trajectories.

The method comprises the following steps which may be implemented as a computer-implemented method:

1. Generating a view of the trajectories and surrounding tissue that is centered and takes its origin in the target region.
2. Displaying the results of the trajectory calculations as a fish-eye projection (similar to visualizations of the stars and planets as viewed from earth).
3. The trajectories are displayed as circles, as they are rays leading away from the target area.
4. Non-critical and critical structures are visualized with different colors and light intensities.
5. In order to preserve the viewer's orientation, an outline of recognizable structures is displayed (e.g. eyes, ears, neck, etc.)
6. To further enhance the orientation, the view can be displayed as a 3D stereoscopic view.
7. For a wide-angle visualization of the trajectories, a three-dimensional stereoscopic virtual reality glasses can be used.

The invention claimed is:

1. A computer-implemented method for determining a trajectory through an anatomical body part for a medical procedure the method executed by one or more processors, the steps comprising:
    acquiring, by one or more of the processors, patient image data describing a medical image of a patient anatomical body part being the anatomical body part in a patient's body;
    acquiring, by one or more of the processors, atlas trajectory data describing a model anatomical body part being a model of the patient anatomical body part, and describing the position of at least one predetermined trajectory through the model anatomical body part;
    acquiring, by one or more of the processors, critical structure data describing the position of at least one critical structure in the model anatomical body part or in the patient anatomical body part;
    determining, by one or more of the processors and based on the patient image data and the atlas trajectory data and the critical structure, mapping data describing a mapping of the model anatomical body part, of the position of the at least one predetermined trajectory and of the position of the at least one critical structure onto the medical image of the patient anatomical body part;
    determining, by one or more of the processors and based on the mapping data and the atlas trajectory data and the patient image data, analysis region data describing an analysis region in the patient image data, the analysis region having a position in the patient anatomical body part fulfilling a predetermined spatial condition relative to the position of the mapped predetermined trajectory;
    determining, by one or more of the processors and based on the patient image data and the atlas trajectory data and the analysis region data and the critical structure data, straight trajectory data describing a straight line trajectory through the patient anatomical body part having a position fulfilling a predetermined spatial condition relative to the position of at least one critical structure in the patient anatomical body part.

2. The method according to claim 1, wherein the atlas trajectory data has been generated on the basis of medical image data and describes an association of image color values with different types of anatomical tissue, and wherein the patient image data describes the medical image as a composition of image colour values for example on a colour scale comparable to the colour scale used for the image colour values described by the atlas trajectory data.

3. The method according to claim 1, wherein the mapping data is determined by applying an image fusion algorithm to the atlas trajectory data and the patient image data by fusing the atlas trajectory data to the patient image data, and determining, by at least one of the processors and based on the mapping between the atlas trajectory data and the patient image data, a mapping between the position of at least one critical structure in the model anatomical body part and a position of at least one corresponding critical structure in the patient anatomical body part.

4. The method according to claim 1, comprising:
    acquiring, by one or more of the processors, analysis region condition data describing the predetermined spatial condition for the position of the analysis region relative to the position of the mapped predetermined trajectory,
    wherein the analysis region data is determined, by one or more of the processors, based on the analysis region condition data.

5. The method according to claim 1, wherein the predetermined trajectory defines a trajectory from a position of a model entry point into the model anatomical body part corresponding to an entry point into the patient anatomical body part to a position of a model target region in the model anatomical body part, wherein the model target region corresponds to a target region in the patient anatomical body part comprising a target of the medical procedure, and wherein the straight line trajectory defines a trajectory from a position of an entry point into the patient anatomical body part to a position of the target region in the patient anatomical body part.

6. The method according to claim 5, wherein the analysis region is determined by mapping, by one or more of the processors, the predetermined trajectory onto the medical image of the patient anatomical body part; and determining, by one or more of the processors and for each incremental point along the mapped predetermined trajectory, an envelope around the mapped predetermined trajectory having a predetermined distance from the incremental point.

7. The method according to claim 5, wherein the analysis region is determined by mapping, by one or more of the processors, the predetermined trajectory onto the medical image of the patient anatomical body part, and one of the following:

determining, by one or more of the processors, a cone in the medical image of the patient anatomical body part, the cone having a conical surface and a tip, wherein the tip of the cone lies at the position of the target region, wherein a straight line connecting the position of the entry point and the position of the target region lies in the conical surface, or wherein the longitudinal axis of the cone lies on a straight line connecting the position of the entry point and the position of the target region, and wherein the cone angle is defined such that the at least one predetermined trajectory lies inside the cone and/or on the conical surface;

determining, by one or more of the processors, a pyramid in the medical image of the patient anatomical body part, the pyramid having a pyramidal surface and a tip, wherein the tip of the pyramid lies at the position of the target region, wherein a straight line connecting the position of the entry point and the position of the target region lies in the pyramidal surface, or wherein the longitudinal axis of the pyramid lies on a straight line connecting the position of the entry point and the position of the target region, and wherein the opening angle of the pyramid at the tip of the pyramid is defined such that the mapped at least one predetermined trajectory lies inside the pyramid and/or on the pyramidal surface.

8. The method according to claim 5, wherein the analysis region is determined by mapping, by one or more of the processors, the predetermined trajectory onto the medical image of the patient anatomical body part, and one of the following:

determining, by one or more of the processors and starting from the position of the target region in the patient anatomical body part and for each incremental point along the mapped predetermined trajectory until the position of the entry point is reached, a cone in the medical image of the patient anatomical body part, the cone having a tip lying at the position of the target region and extending at least substantially to a surface of the patient anatomical body part in which the position of the entry point lies, so that the incremental point lies inside the cone and/or on the conical surface;

determining, by one or more of the processors and starting from the position of the target region in the patient anatomical body part and for each incremental point along the mapped predetermined trajectory until the position of the entry point is reached, a pyramid in the medical image of the patient anatomical body part, the pyramid having a pyramidal surface and a tip, the tip lying at the position of the target region and extending at least substantially to a surface of the patient anatomical body part in which the position of the entry point lies, so that the incremental point lies inside the pyramid and/or on the pyramidal surface.

9. The method according to claim 1, wherein the critical structure is an anatomical structure to be avoided by the medical procedure and wherein the critical structure data is acquired based on information defining the medical procedure.

10. The method according to claim 1, comprising:

acquiring, at one or more of the processors, straight trajectory condition data describing the predetermined spatial condition for the position of the straight line trajectory relative to the position of the at least one critical structure in the patient anatomical body part corresponding to the critical structure in the model anatomical body part, wherein the straight trajectory data is determined, by one or more of the processors, further based on the straight trajectory condition data.

11. The method according to claim 1, wherein the straight trajectory data is determined by mapping, by one or more of the processors, the predetermined trajectory onto the medical image of the patient anatomical body part; and determining, by one or more of the processors, a straight line lying inside the analysis region having a predetermined distance from the mapped predetermined trajectory and at least one critical structure in the patient anatomical body part corresponding to at least one critical structure in the model anatomical body part, wherein the straight line is determined by using an optimisation algorithm.

12. At least one non-transient computer storage medium storing instructions for determining a trajectory through an anatomical body part for a medical procedure, the instructions comprising:

a plurality of instructions which, when executed by the one or more processors, causes the one or more processors to:

acquire, by one or more of the processors, patient image data describing a medical image of a patient anatomical body part being the anatomical body part in a patient's body;

acquire, by one or more of the processors, atlas trajectory data describing a model anatomical body part being a model of the patient anatomical body part, and describing the position of at least one predetermined trajectory through the model anatomical body part;

acquire, by one or more of the processors, critical structure data describing the position of at least one critical structure in the model anatomical body part or in the patient anatomical body part;

determine, by one or more of the processors and based on the patient image data and the atlas trajectory data and the critical structure, mapping data describing a mapping of the model anatomical body part, of the position of the at least one predetermined trajectory and of the position of the at least one critical structure onto the medical image of the patient anatomical body part;

determine, by one or more of the processors and based on the mapping data and the atlas trajectory data and the patient image data, analysis region data describing an analysis region in the patient image data, the analysis region having a position in the patient anatomical body part fulfilling a predetermined spatial condition relative to the position of the mapped predetermined trajectory;

determine, by one or more of the processors and based on the patient image data and the atlas trajectory data and the analysis region data and the critical structure data, straight trajectory data describing a straight line trajectory through the patient anatomical body part having a position fulfilling a predetermined spatial condition relative to the position of at least one critical structure in the patient anatomical body part.

13. A system for determining a trajectory through an anatomical body part, the trajectory being usable for a medical procedure, the system comprising:

memory storing instructions;

one or more processors executing the instructions stored in the memory to:

acquire, by one or more of the processors, patient image data describing a medical image of a patient anatomical body part being the anatomical body part in a patient's body;

acquire, by one or more of the processors, atlas trajectory data describing a model anatomical body part being a model of the patient anatomical body part, and describing the position of at least one predetermined trajectory through the model anatomical body part;

acquire, by one or more of the processors, critical structure data describing the position of at least one critical structure in the model anatomical body part or in the patient anatomical body part;

determine, by one or more of the processors and based on the patient image data and the atlas trajectory data and the critical structure, mapping data describing a mapping of the model anatomical body part, of the position of the at least one predetermined trajectory and of the position of the at least one critical structure onto the medical image of the patient anatomical body part;

determine, by one or more of the processors and based on the mapping data and the atlas trajectory data and the patient image data, analysis region data describing an analysis region in the patient image data, the analysis region having a position in the patient anatomical body part fulfilling a predetermined spatial condition relative to the position of the mapped predetermined trajectory;

determine, by one or more of the processors and based on the patient image data and the atlas trajectory data and the analysis region data and the critical structure data, straight trajectory data describing a straight line trajectory through the patient anatomical body part having a position fulfilling a predetermined spatial condition relative to the position of at least one critical structure in the patient anatomical body part.

* * * * *